United States Patent [19]

Kapil et al.

[11] Patent Number: 5,124,358
[45] Date of Patent: Jun. 23, 1992

[54] EFFECT OF TRANSGLUTAMINASE INHIBITION ON MICROFILARIAE DEVELOPMENT AND MACROFILARIAE VIABILITY

[75] Inventors: Mehta Kapil, Houston, Tex.; Undaru R. Rao; Ann C. Vickery, both of Tampa, Fla.

[73] Assignee: The Board of Reagents The University of Texas System, Austin, Tex.

[21] Appl. No.: 466,127

[22] Filed: Jan. 16, 1990

[51] Int. Cl.⁵ .................. A01N 33/02; A01N 41/06; A61K 31/13; A61K 31/18
[52] U.S. Cl. .................. 514/603; 514/400; 514/663; 514/673
[58] Field of Search .......... 514/603, 400, 663, 673

[56] References Cited

U.S. PATENT DOCUMENTS 4,396,628 8/1983 Pastan et al. .................. 514/603

OTHER PUBLICATIONS

Noble et al.; Parasitology, 2nd (1964) pp. 264-265, 270-273, 326, 327 and 350-363.

Primary Examiner—Allen J. Robinson
Attorney, Agent, or Firm—Arnold, White and Durkee

[57] ABSTRACT

A method is described for blocking maturation and production of microfilariae in adult filarial nematodes utilizing a transglutaminase inhibitor, such as monodansyl cadaverine (MDC). Experiments applying this method to several Brugia filarial infections, including *Brugia malayi*, were successful. Higher concentration of transglutaminase inhibitor proved to be filariacidal.

18 Claims, 3 Drawing Sheets

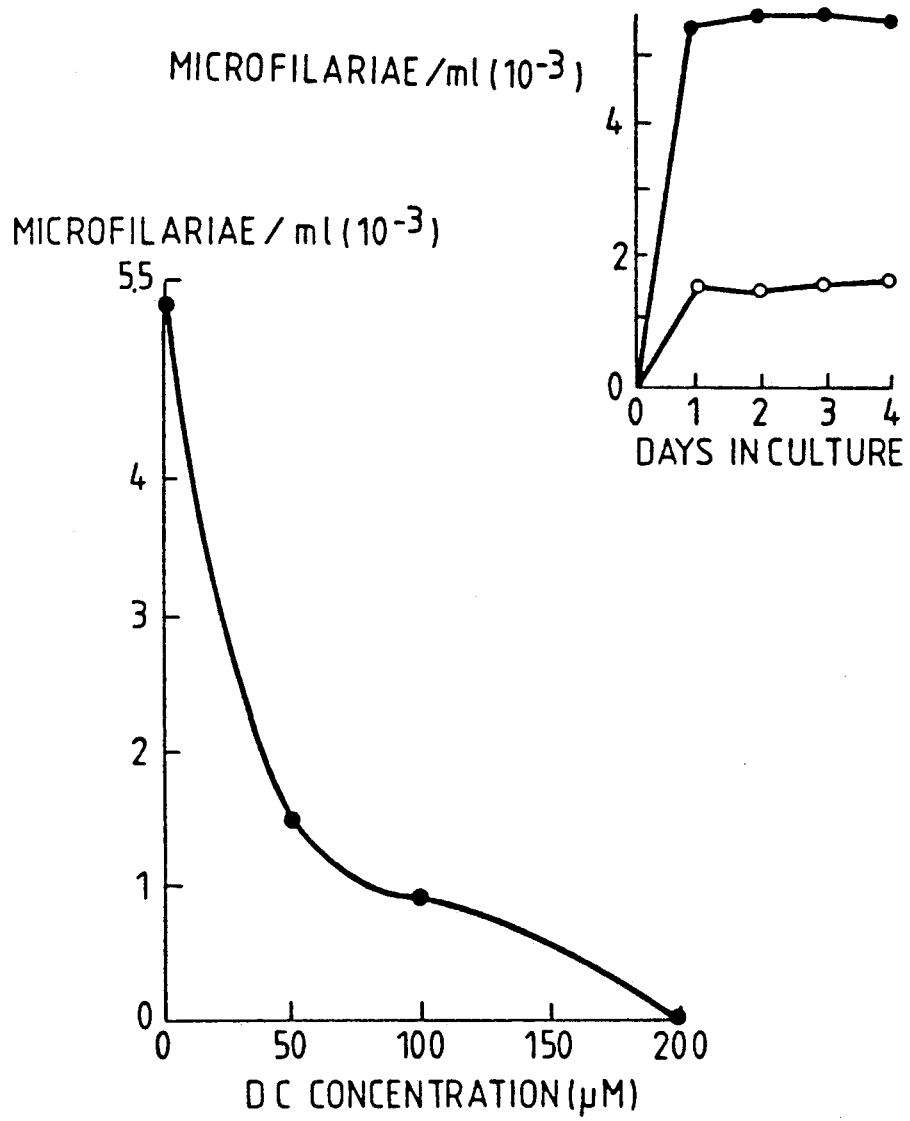

FIG.1B
FIG.1C
FIG.2A
kD
130►
75►
50►
39►
27►
17►
1 2 3 4 5
FIG.2B
►
►
►
►
►
►
1 2 3
FIG.2C
1 2 3 4 5

EFFECT OF TRANSGLUTAMINASE INHIBITION ON MICROFILARIAE DEVELOPMENT AND MACROFILARIAE VIABILITY

The government may own certain rights in the present invention pursuant to N.I.H. grants CA 38751 and AI 20052.

BACKGROUND OF THE INVENTION

The present invention relates to a novel method for blocking the maturation and production of microfilariae in an adult female filarial nematode comprising inhibiting the transglutaminase activity in the nematode by treatment with a transglutaminase inhibitor. Moreover, this invention has not only in vitro application but in vivo application for preventing the development of mature microfilariae of *Brugia malayi* and other filarial nematodes in a mammalian host by administration of a pharmacologically acceptable concentration of a transglutaminase inhibitor, monodansyl cadaverine, to the host. At higher concentrations the same transglutaminase inhibitor is filariacidal. Thus, transglutaminase inhibitors, especially monodansyl cadaverine, may play an important role in treating filariasis and thus helping to prevent the spread of these parasitic diseases.

Filariasis is a group of disorders produced by infection with threadlike nematodes of the superfamily Filarioidea. These nematodes invade the lymphatics and subcutaneous and deep tissues of the host, even causing blindness. The viviparous female discharges microfilariae into the blood or subcutaneous tissues where they live for weeks or months until they are taken up by hematophagous arthropods. Within these arthropod vectors the microfilariae metamorphose into the infective third-stage larvae ($L_3$) in a period of several weeks. The $L_3$ larvae migrate to the mouthparts of the arthropod vector and infect a new host when the arthropod takes another blood meal. The $L_3$ larvae mature into adult nematodes over a period of several months and the fertilized females begin producing microfilariae, thus completing the cycle (1).

Nearly four hundred million people worldwide suffer from chronic infections caused by filarial nematodes (2). Filariasis is a major cause of morbidity in endemic areas of Africa, Asia, the Middle East, Pacific Islands, Central and South America, Mexico and the West Indies. Some of the more common types of filariasis are: Lymphatic filariasis produced by *Wuchereria bancrofti, Brugia malayi* and *Brugia timori* which causes lymphatic blockade and elephantiasis; Loiasis produced by *Loa loa,* also known as African Eye Worm, characterized by transient subcutaneous (Calabar) swellings as the adult nematodes migrate under the skin, including the conjunctiva of the eye; and Onchocerciasis or River Blindness, produced by *Onchocerca volvulus,* a cutaneous filariasis causing pruritic skin rash, sclerosing lymphadenitis, subcutaneous nodules and ocular lesions often leading to blindness (3,9). Gravid female nematodes can live as long as fifteen years within a host releasing thousands of microfilariae a day. The present chemotherapeutic treatments are unsatisfactory as most of them are inefficacious against the mature parasites while being microfilariacidal and frequently induce a severe allergic response to the death of the microfilariae known as the Mazzotti reaction. This allergic response can sometimes be fatal or in patients with *Onchocerca volvulus* may lead to the development of permanent eye lesions and blindness (4). Control of vectors has not proved to be sufficiently effective to interrupt transmission of the parasites.

An important discovery was made by the present inventors. They discovered that a pharmaceutically acceptable transglutaminase inhibitor, for example, monodansyl cadaverine, could prevent the formation of fully developed microfilariae in utero in adult female filarial nematodes by inhibiting a particular transglutaminase found in these female nematodes. Thus monodansyl cadaverine, administered parenterally, or possibly enterally, offers a means of treatment of filariasis in humans while avoiding the side effects of toxicity or allergic response to drug therapy. A discussion of the methods and applications of the present invention can be found in the present disclosure.

Abbreviations used herein include:

$L_3$ infective third-stage larvae
MDC monodansyl cadaverine [N- (5-aminopentyl) -5-dimethylamino-1-naphthalenesulfonamide]
DDC dimethyl-dansyl cadaverine
ul microliter
FCS fetal calf serum
Mf microfilariae
ml milliliter
uM micromolar
mM millimolar
EDTA ethylenediamine tetraacetic acid
EGTA ethylene glycol (2-aminoethyl ether) tetraacetic acid
CHAPS 3- [(3-cholamidopropyl) dimethylammino]-1-propane sulfonate
SDS sodium dodecylsulfate
PAGE polyacrylamide gel electrophoresis
CUB-7401 monoclonal antibody against guinea pig liver tissue transglutaminase
FITC fluorescein isothiocyanate
PBS phosphate buffered saline
IgG immunoglobulin G
UV ultraviolet light
IP intraperitoneally
Kg kilogram
mg milligram
IV intravenously
$CO_2$ carbon dioxide

SUMMARY OF THE INVENTION

The present invention provides a method for blocking maturation and production of microfilariae in an adult female filarial nematode comprising treating said nematode with a transglutaminase inhibitor which inhibits the transglutaminase activity of an adult female filarial nematode. This method, for example, more specifically blocks maturation and production of microfilariae in an adult female filarial nematode of organisms which include *Brugia malayi, Brugia pahangi* or *Brugga patei* and comprises treating said nematode with a transglutaminase inhibitor which inhibits the transglutaminase activity of the adult female filarial nematode. Of course, this method would also be applicable to other filarial nematode infections such as *Brugia timori, Wuchereria bancrofti, Loa loa* or *Onchocerca volvulus.*

In one embodiment, blocking maturation and production of microfilariae in an adult female filarial nematode of *Brugia malayi, Brugia pahangi* or *Brugia patei* is accomplished by an in vitro method comprising treating said nematode with a transglutaminase inhibitor to inhibit the transglutaminase activity of an adult female filarial nematode.

One transglutaminase inhibitor utilized in this invention is monodansyl cadaverine [N- (5-aminopentyl)-5-dimethylamino-1-naphthalenesulfonamide] but other transglutaminase inhibitors or pseudo-substrates of transglutaminase are understood to be included in the category termed transglutaminase inhibitor.

The concentration of transglutaminase inhibitor used to block maturation and production of microfilariae in an adult female filarial nematode is about a two hundred micromolar concentration but it may ba possible to employ other concentrations of transglutaminase inhibitor especially if an inhibitor other than monodansyl cadaverine [N- (5-aminopentyl)-5-dimethylamino-1-naphthalenesulfonamide] is utiized.

In another embodiment, a method for killing an adult filarial nematode comprises treating said nematode with a transglutaminase inhibitor, for example, monodansyl cadaverine, in a greater than about three hundred micromolar concentration. This method would pertain to all the filarial infections previously listed.

In a more preferred embodiment, the present invention involves a method for blocking maturation and production of microfilariae in an adult female nematode existing within a mammalian host. This comprises treating the mammalian host with a transglutaminase inhibitor in an amount sufficient to inhibit the transglutaminase activity of an adult female filarial nematode.

Another preferred embodiment provides a method for blocking maturation and production of microfilariae in an adult female *Brugia malayi* nematode existing within a mammalian host comprising treating the mammalian host with a transglutaminase inhibitor in an amount sufficient to inhibit the transglutaminase activity of an adult female *Brugia malayi* nematode.

The transglutaminase inhibitor used to block production of mature microfilariae in an adult female filarial nematode existing within a mammalian host, including the *Brugia malayi* nematode, is most preferably monodansyl cadaverine [N-(5-aminopentyl)-5-dimethylamino-1-naphthalenesulfonamide] and most preferably in an about two hundred micromolar concentration, but this choice of transglutaminase inhibitor and concentration may be subject to the provisions previously stated.

In another embodiment, this invention provides a method for treating filariasis in a mammalian host comprising administering a transglutaminase inhibitor to the host in an amount sufficient to kill the adult filarial nematodes producing the filarial infection. Onchocerciasis and Loiasis would be along the filarial infections to be treated by this method.

Another preferred embodiment, a method for treating lymphatic filariasis in a mammalian host, comprises administering to the host a transglutaminase inhibitor in an amount sufficient to kill the adult filarial nematodes producing the lymphatic filariasis. This method which may be utilized for treating a specific type of lymphatic filariasis comprises administering to a mammalian host a transglutaminase inhibitor in an amount sufficient to kill the adult *Brugia malayi* nematodes producing the lymphatic filariasis. This method may also be used in treating lymphatic filariasis produced, for example, by *Brugia timori, Brugia pahangi, Brugia patei* or *Wuchereria bancrofti.*

The transglutaminase inhibitor administered to a mammalian host to treat filariasis or lymphatic filariasis is most preferably monodansyl cadaverine [N-(5-aminopentyl)-5-dimethylamino-1-naphthalenesulfonamide] and is subject to the previously stated provisions.

The mode of administration of the transglutaminase inhibitor to a mammalian host may be parenteral, for example intravascular or more specifically intravenous. The transglutaminase inhibitor might even be supplied on a continuous dose basis transdermally via a skin patch or given enterally. Depending upon the clearance rate of the transglutaminase inhibitor within the mammalian host, daily, weekly or perhaps even a monthly dose regimen could be followed in treating the filariasis.

The mammalian host to which the transglutaminase inhibitor is administered for treatment of filariasis or for blocking maturation and production of microfilariae in an adult filarial nematode, within said host, may be a rodent, a dog, cat or primate such as a monkey or a human.

In another preferred embodiment, this invention provides a pharmaceutical formulation for treating filariasis in a mammalian host comprising a transglutaminase inhibitor, in an amount sufficient to kill adult filarial nematodes producing the filariasis, in combination with an acceptable pharmaceutical excipient. Filarial infections within a mammalian host such as: *Onchocerca volvulus, Loa loa, Wuchereria bancrofti, Brugia timori, Brugia pahangi* or *Brugia patei,* may all be treated with such a pharmaceutical formulation.

In yet another preferred embodiment, a pharmaceutical formulation is provided for treating lymphatic filariasis specifically produced by *Brugia malayi* in a mammalian host comprising a transglutaminase inhibitor in an amount sufficient to kill adult *Brugia malayi* nematodes producing the lymphatic filariasis, in combination with a pharmaceutically acceptable excipient.

In the last two preferred embodiments, monodansyl cadaverine [N-(5-aminopentyl)-5-dimethylamino-1-naphthalenesulfonamide], is the transglutaminase inhibitor of choice but other such inhibitors or pseudo-substrates may be used in the pharmaceutical formulation as previously discussed in the provisions for transglutaminase inhibitors. It is also understood that the mammalian hosts to which the pharmaceutical formulations are applied are the same as previously mentioned: a rodent, dog, cat or primate such as a monkey or a human.

These and other aspects of the present invention will become more readily apparent when viewed in the context of the description of specific embodiments in the examples set forth below. However., neither the summary, the description or the examples are intended to limit the scope of the claims unless expressly stated therein.

BRIEF DESCRIPTION OF THE DRAWINGS

FIG. 1A is a dose response curve showing the effect of increasing concentration of monodansyl cadaverine (DC) (a transglutaminase inhibitor) on the release of microfilariae by *Brugia malayi* adult female nematodes. The results shown are the average number of microfilariae released by two female nematodes from four independent experiments. The standard deviation was less than ten percent. FIG. 1AA: The average number of microfilariae released into the spent medium by two *Brugia malayi* female nematodes over one to four days of incubation in the absence of fifty micromolar monodansyl cadaverine (MDC) (solid circle) or presence of fifty micromolar monodansyl cadaverine (MDC) (open circle).

FIG. 1B demonstrates the morphology of the developing embryos in the uterus of the *Brugia malayi* female nematode as seen under phase-contrast microscopy (X400) after three days of incubation in RPMI 1640 medium.

FIG. 1C demonstrates the morphology of the developing embryos in the uterus of the *Brugia malayi* female nematode as seen under phase-contrast microscopy (X400) after three days of incubation in RPMI 1640 medium containing 200 micromolar monodansyl cadaverine (MDC). Embryos are lesser in number and are undifferentiated.

FIG. 2A demonstrates the detection of transglutaminase by immunoblotting in soluble and insoluble extracts of adult female *Brugia malayi* and the absence of the enzyme in the male adult nematodes of same species. Immunodetection of transglutaminase on nitrocellulose paper was performed using anti-tissue transglutaminase monoclonal antibody (CUB 7401) and alkaline-phosphatase-coupled goat antibody to mouse immunoglobulin G as second antibody. Lane 1: Molecular weight markers; Lane 2: purified guinea pig liver transglutaminase (1 microgram); Lane 3: extracts from male nematodes; Lane 4: soluble extracts from female nematodes; Lane 5: insoluble extracts from female nematodes.

FIG. 2B shows the immunoprecipitation of the protein extracts from adult male and female *Brugia malayi* nematodes. SDS-gel electrophoresis of CUB 7401 immunoprecipitated soluble and insoluble extracts of the male and female adult nematodes were detected by fluorography. Lane 1: immunoprecipitate of soluble extracts of male nematodes; Lane 2: immunoprecipitate of soluble extracts of female nematodes; Lane 3: immunoprecipitate of insoluble extracts of female nematodes.

FIG. 2C indicates the total protein profiles of the adult *Brugia malayi* nematodes. SDS-gel electrophoresis fractions of soluble and insoluble protein extracts of adult female and male nematodes were subjected to continuous PAGE fractionation followed by Coomassie blue protein staining. Lane 1: purified guinea pig liver transglutaminase (5 micrograms); Lane 2: soluble fraction of adult male nematodes; Lane 3: soluble fraction of adult female nematodes; Lane 4: insoluble fraction of female nematodes; Lane 5: molecular weight markers.

FIG. 3A shows the immunofluorescence under a Leitz phase-contrast microscope and FIG. 3B shows the immunofluorescence under a fluorescence microscope (40× objective).

FIG. 4A shows that the number and the amount of substrate proteins is much higher in the female nematodes than in the male nematodes as visualized by SDS polyacrylamide-gel electrophoresis under UV light. Lane 1: Molecular weight markers; Lane 2: Guinea pig liver transglutaminase, extracts of adult male nematodes, 400 micromolar monodansyl cadaverine (MDC) and calcium chloride; Lane 3: Guinea pig liver transglutaminase, extracts of female nematodes, 400 micromolar monodansyl cadaverine (MDC) and calcium chloride; Lane 4: Guinea pig liver transglutaminase, extracts of male nematodes, 400 micromolar monodansyl cadaverine (MDC and EGTA; Lane 5: Guinea pig liver transglutaminase, extracts of female nematodes, 400 micromolar MDC and EGTA; Lane 6: Endogenous transglutaminase from adult female nematodes with 200 micromolar monodansyl cadaverine (MDC ; Lane 7: untreated adult female nematode extracts as the control.

FIG. 4B is the Coomassie blue stained gel of the protein samples shown in FIG. 4A.

DETAILED DESCRIPTION OF THE PREFERRED EMBODIMENT

Figure 3A:
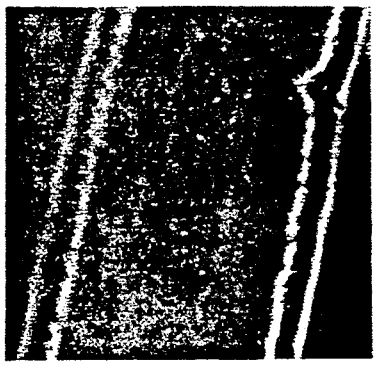
FIGS. 3A and 3B demonstrate indirect immunofluorescence labeling of the *Brugia malayi* adult female nematode using CUB 7401 antibody.

This patent describes a method for blocking the maturation and production of microfilariae in adult female filarial nematodes by inhibiting the transglutaminase activity of the nematodes. It also describes the filariacidal capabilities of transglutaminase inhibitors, especially monodansyl cadaverine. The inventors have shown that a 22 kD transglutaminase found only in the adult female filarial nematode is essential for the differentiation of the early embryonic stages to the mature microfilariae in utero.

Monodansyl cadaverine (MDC) was found to be the most effective transglutaminase inhibitor among those tested for blocking the maturation and production of microfilariae in vitro in three different Brugia species which cause lymphatic filariasis, *Brugia malayi, Brugia pahangi* and *Brugia patei*. MDC inhibition proceeded in a dose dependent manner. Of course, monodansyl cadaverine may not be the only transglutaminase inhibitor or pseudo-substrate that can be utilized in this capacity. All such pseudo-substrates are considered to fall within the scope of this invention. Also there is no reason to limit the application of monodansyl cadaverine only to these aforementioned Brugia infections as it may be applicable to control of other filarial infections such as lymphatic filariasis caused by *Wuchereria bancrofti* and *Brugia timori, Loiasis* and *Onchocerciasis*.

Experiments with intraperitoneally transplanted *Brugia malayi* adult nematodes in nude mice indicated that treatment of a mammalian host intravenously with a transglutaminase inhibitor, specifically monodansyl cadaverine, could cause the death of the filarial nematodes while leaving the host free of toxic symptoms. The dose of transglutaminase inhibitor, MDC, given in vivo, was about five times as concentrated as was necessary to inhibit maturation and production of microfilariae in utero in adult female nematodes.

Toxicity studies with monodansyl cadaverine and CD-1 mice showed that concentration levels of the inhibitor which produced even the slightest evidence of toxicity far exceeded the dose level necessary to inhibit microfilariae production in vitro.

Although in vivo experiments have only been performed on mice, there is no reason to believe that the application of monodansyl cadaverine, or perhaps another transglutaminase inhibitor or pseudo-substrate, to the treatment of filariasis in other mammalian hosts is not possible. This method should be acceptable in cats, dogs, primates and especially humans for treatment of filarial infections.

While the in vivo experiments were performed by administering the transglutaminase inhibitor, monodansyl cadaverine, intravenously to a mammalian host, this should not limit the mode of administration of the drug. Any type of parenteral mode of administration, such as intravascular, intraarterial or even via a transdermal patch might prove to be just as effective a means of drug delivery. Another possible mode of administration of a transglutaminase inhibitor, could be enteral, as there is no reason to believe that it, e.g. monodansyl cadaverine, would be broken down in the gastrointestinal tract and it should be readily absorbed into the circulatory system.

Acceptable pharmaceutical formulations with compatible therapeutic regimen for a transglutaminase inhibitor, such as monodansyl cadaverine, can be easily developed by those of skill in the pharmaceutical and medical arts with the aid of the present disclosure.

The following examples are presented to describe preferred embodiments and utilities of the present invention but should not be construed as limiting the claims thereof.

of streptomycin. Two female nematodes were incubated, each, in one milliliter of this medium containing the desired concentration of the transglutaminase pseudo-substrate (inhibitor) for the required number of days at thirty-seven degrees Celsius in an atmosphere of five percent carbon dioxide and ninety-five percent air. Adult *Brugia malayi* nematodes were examined daily for a period of four days for viability. Various pseudo-substrates: monodansyl cadaverine (MDC)(5), a known high affinity pseudo-substrate of transglutaminase; dimethyl-dansyl cadaverine (DDC), an inactive analogue of MDC; methylamine; putrescine and histamine, were tested at varying concentrations. As Table I indicates only monodansyl cadaverine, at about 300 micromolar concentration and putrescine, at about 20 millimolar concentration, produced death in the female nematodes. Each experiment was performed in duplicate.

TABLE I

Effect of MDC, DDC, Methylanime, Putrescine and Histamine on *Brugia malayi* adult female nematode viability in vitro.

| Concentration | MDC | | | | | DDC | | | |
|---|---|---|---|---|---|---|---|---|---|
| | Day | 1 | 2 | 3 | 4 | Day | 1 | 2 | 3 | 4 |
| 50 uM | | ++ | ++ | ++ | ++ | | ++ | ++ | ++ | ++ |
| 100 uM | | ++ | ++ | ++ | ++ | | ++ | ++ | ++ | ++ |
| 200 uM | | ++ | ++ | ++ | ++ | | ++ | ++ | ++ | ++ |
| 300 uM | | − | − | − | − | | ++ | ++ | ++ | ++ |
| 500 uM | | − | − | − | − | | N.D. | | | |

| Concentration | Methylamine | | | | Putrescine | | | | Histamine | | | |
|---|---|---|---|---|---|---|---|---|---|---|---|---|
| | Day | 1 | 2 | 3 | 4 | 1 | 2 | 3 | 4 | 1 | 2 | 3 | 4 |
| 5 mM | | ++ | ++ | ++ | ++ | ++ | ++ | ++ | ++ | ++ | ++ | ++ | ++ |
| 10 mM | | ++ | ++ | ++ | ++ | ++ | ++ | ++ | ++ | ++ | ++ | ++ | ++ |
| 20 mM | | ++ | ++ | ++ | + | − | − | − | − | + | + | + | + |

Grading ++, Alive and very active. +, Alive but inactive (Less mobile); −, completely immobile
Inhibitors were used at the required concentration in RPMI 1640 and 10% FCS (fetal calf serum).
Results from a single experiment in duplicate.
Two adult female nematodes were incubated for each concentration.
MDC—monodansyl cadaverine
DDC—dimethyl-dansylcadaverine
Adult nematodes were recovered from the peritoneal cavity of *Brugia malayi* infected jirds. Two nematodes were incubated for each concentration in duplicate at 37° C. and in an atmosphere of 5% CO₂ and 95% air.
N.D.—not determined

EXAMPLE I

In Vitro Inhibition of the Formation of Microfilariae

A novel transglutaminase was identified in adult filarial nematodes of *Brugia malayi*. Incubation of the gravid female nematodes in the presence of various possible pseudo-substrates (inhibitors) for the novel transglutaminase were studied not only in *Brugia malayi* but in *Brugia pahangi* and *Brugia patei* as well. The following example sets forth the preferred in vitro method for blocking the formation of microfilariae in adult female filarial nematodes.

A. Effect of Known Pseudo-substrates for Transglutaminases on Adult Female Nematode Viability Various known pseudo-substrates (inhibitors) for transglutaminases were investigated for their effect on viability of adult female *Brugia malayi* nematodes. Varying concentrations of each pseudo-substrate were tested over a four-day period.

Adult female *Brugia malayi* nematodes were obtained from the peritoneal cavities of one hundred-twenty-day old infected Mongolian jirds, (*Meriones unguiculatus*), rinsed thoroughly in RPMI 1640 medium which was supplemented with ten percent fetal calf serum, twenty millimolar hepes buffer, one hundred units per milliliter of penicillin and one hundred micrograms per milliliter

B. Effect of Known Pseudo-substrates for Transglutaminases on the Release of Microfilariae from *Brugia malayi*

The effect of monodansyl cadaverine (MDC), dimethyldansyl cadaverine (DDC), methylamine, putrescine and histamine on microfilariae release by *Brugia malayi* in vitro was studied. Adult female *Brugia malayi* nematodes obtained and treated as in Example IA were incubated in one milliliter each of the same medium either with or without varying concentrations of one of the following transglutaminase pseudo-substrates (inhibitors): monodansyl cadaverine, methylamine, putrescine, histamine or dimethyl-dansyl cadaverine, the inactive analog of MDC, with or without ten percent fetal calf serum. Two nematodes were incubated for each concentration in duplicate at thirty-seven degrees Celsius in an atmosphere of five percent carbon dioxide and ninety-five percent air. After a twenty-four hour incubation period, the parasites were removed and ten microliters of the spent medium was examined under the light microscope to count the microfilariae. A similar procedure was followed after a forty-eight, seventy-two or ninety-six hour incubation period. These results are the average number of microfilariae released by two female nematodes from four independent experiments. The standard deviation from the mean was less than ten percent. The results for monodansyl cadaverine incubation can be seen in Table II and are plotted in FIG. 1A. Incubation with two hundred micromolar concentration of monodansyl cadaverine (MDC) or greater prevents mature microfilariae production. The INSET of FIG. 1A indicates the more than threefold reduction of microfilariae by a only fifty micromolar concentration of monodansyl cadaverine. FIG. 1B and FIG. 1C illustrate the effect of medium alone versus medium containing a two hundred micromolar concentration of monodansyl cadaverine on developing embryos in utero in *Brugia malayi*. FIG. 1B shows the sheathed embryos differentiating in culture medium and FIG. 1C shows the lack of a sheath and lack of differentiation in the developing embryos due to the presence of monodansyl cadaverine.

TABLE II

Effect of MDC on Mf release in vitro by *Brugia malayi* female nematodes

| MDC | 10% FCS | Mf counts in 1 ml of spent medium (Mean of 2 experiments in duplicate) Days of incubation | | | |
|---|---|---|---|---|---|
| | | Day 1 | Day 2 | Day 3 | Day 4 |
| 0 (Control) | − | 3800 | 4000 | 4120 | 4000 |
| | + | 5400 | 5800 | 5600 | 5500 |
| 50 uM | − | 600 | 670 | 710 | 760 |
| | + | 1500 | 1400 | 1500 | 1600 |
| 100 uM | − | 300 | 270 | 260 | 240 |
| | + | 1600 | 1400 | 1500 | 1500 |
| 200 uM | − | 0 | 0 | 0 | 0 |
| | + | 46 | 50 | 50 | 48 |
| 300 uM | − | 0 | 0 | 0 | 0 |
| | + | 0 | 0 | 0 | 0 |

(All nematodes were inactive, immobile and slowly killed)

Adult worms were recovered from the peritoneal cavity of *Brugia malayi* infected jirds. Two worms were incubated for each concentration in duplicate and incubated at 37° C. in an atmosphere of 5% CO₂ and 95% air. Mf counts were taken in 10 ul of spent medium and calculated for 1 ml.
FCS—fetal calf serum
Mf—microfilariae
MDC—monodansyl cadaverine
− without 10% fetal calf serum
+ with 10% fetal calf serum The results of the incubation of adult female *Brugia malayi* nematodes with dimethyl-dansyl cadaverine (DDC), a structurally related analog of MDC, in varying concentrations can be seen in Table III. Dimethyl-dansyl cadaverine, which does not inhibit transglutaminase activity, failed to inhibit microfilariae maturation and production in vitro in *Brugia malayi*.

The results for the incubation of adult female *Brugia malayi* nematodes with varying concentration of methylamine, putrescine and histamine can be seen in Table IV. It is felt that the data collected after Day 1 is skewed. These particular transglutaminase pseudo-substrates after the first twenty-four hours actually become physiological substrates and are metabolized by the adult nematodes and no longer function as competitive inhibitors. Histamine showed the most promising effects of this group of pseudo-substrates but it is not suitable as a pharmaceutical treatment.

Thus, the ability to inhibit microfilariae maturation and production correlated well with the pseudo-substrate's ability to inhibit transglutaminase activity. Monodansyl cadaverine, the most active transglutaminase inhibitor, was the most successful in inhibiting microfilariae maturation and production, and methylamine, the least efficient transglutaminase inhibitor, was least successful in inhibiting production and maturation of microfilariae.

TABLE III

Effect of DDC on Mf release in vitro by *Brugia malayi* female nematodes

| DDC | 10% FCS | Mf counts in 1 ml of spent medium (Mean of 2 experiments in duplicate) Days of incubation | | | |
|---|---|---|---|---|---|
| | | Day 1 | Day 2 | Day 3 | Day 4 |
| 0 (Control) | − | 2900 | 3200 | 3300 | 3300 |
| | + | 2400 | 3600 | 3400 | 3500 |
| 50 uM | − | 2200 | 2300 | 2400 | 2400 |
| | + | 2600 | 2600 | 2500 | 2300 |
| 100 uM | − | 2000 | 2100 | 2000 | 2100 |
| | + | 2500 | 2600 | 2600 | 2500 |
| 200 uM | − | 2400 | 2700 | 2800 | 2600 |
| | + | 2600 | 2800 | 2600 | 2500 |
| 300 uM | − | 2400 | 2400 | 2300 | 2100 |
| | + | 2500 | 2300 | 2200 | 2200 |
| 500 uM | | N.D. | | | |

Adult nematodes were recovered from the peritoneal cavity of *Brugia malayi* infected jirds. Two nematodes were incubated for each concentration in duplicate and incubated at 37° C. in an atmosphere of 5% CO₂ and 95% air. Mf counts were taken in 10 ul of spent medium and calculated for 1 ml.
FCS—fetal calf serum
Mf—microfilariae
DDC—dimethyl-dansyl cadaverine

TABLE IV

Effect of Methylamine, Putrescine and Histamine on Mf release in vitro by *Brugia malayi* adult female nematodes worms

| Concentration | 10% FCS serum | Mf counts/ml of spent medium (Mean of 2 experiments in duplicate) Days of incubation | | | |
|---|---|---|---|---|---|
| | | Day 1 | Day 2 | Day 3 | Day 4 |
| 0 (Control) | − | 2400 | 3000 | 3520 | 3860 |
| | + | 3600 | 3840 | 3800 | 4010 |
| Methylamine | | | | | |
| 5 mM | − | 1050 | 2000 | 2400 | 3280 |
| | + | 1300 | 2880 | 3000 | 3460 |
| 10 mM | − | 1300 | 1280 | 1800 | 2240 |
| | + | 1400 | 2000 | 2200 | 2560 |
| 20 mM | − | 1400 | 1840 | 1900 | 2100 |
| | + | 1700 | 2200 | 2000 | 2100 |
| Putrescine | | | | | |
| 5 mM | − | 1056 | 1520 | 1720 | 2080 |
| | + | 1000 | 2440 | 3000 | 3760 |
| 10 mM | − | 800 | 1120 | 1400 | 2160 |
| | + | 860 | 1280 | 2000 | 2800 |
| 20 mM | − | 200 | Adults became inactive and killed | | |
| | + | 280 | | | |
| Histamine | | | | | |
| 5 mM | − | 950 | 1360 | 2000 | 2840 |
| | + | 1200 | 2400 | 2400 | 3000 |
| 10 mM | − | 300 | 720 | 1000 | 1120 |
| | + | 1250 | 1440 | 1500 | 1920 |
| 20 mM | − | 100 | 240 | 260 | 320 |
| | + | 350 | 560 | 640 | 800 |

Adult nematodes were recovered from the peritoneal cavity of *Brugia malayi* infected jirds. Two nematodes incubated for each concentration in duplicate and incubated at 37° C. in an atmosphere of 5% CO₂ and 95% air. Mf counts were taken in 10 ul of spent medium and calculated for 1 ml.
FCS—fetal calf serum
Mf—microfilariae C. Effect of Pretreatment with Monodansyl cadaverine on Microfilariae Release in Vitro in *Brugia malayi*

Pretreatment of *Brugia malayi* with two hundred micromolar monodansyl cadaverine for twenty-four hours in the RPMI 1640 medium recited in Example IA and followed by transfer to normal medium RPMI 1640 for one to four days without the monodansyl cadaverine, was accomplished.

The results of the pretreatment experiment can be seen in Table V. This experiment indicates that as long as the nematodes are exposed to the non-toxic concentration of monodansyl cadaverine the release and production of microfilariae are inhibited. Once the nematodes are returned to normal medium they begin to release microfilariae irrespective of the period of incubation or pretreatment. As the pseudo-substrate is gradually removed in normal RPMI 1640 medium, transglutaminase inhibition is removed and embryological development of microfilariae resumes.

TABLE V

Effect of pre-incubation of *Brugia malayi* adult nematodes in vitro in MDC (200 uM concentration) and further release of Mf in normal medium (RPMI 1640).

| Pre-incubation time | 10% FCS serum | Mf release in vitro/ml Days after incubation | | | |
|---|---|---|---|---|---|
| | | Day 1 | Day 2 | Day 3 | Day 4 |
| 24 hr | − | 300 | 440 | 1200 | 1600 |
| | + | 700 | 760 | 1450 | 1900 |
| 48 hr | − | 320 | 640 | 800 | 1000 |
| | + | 500 | 600 | 1640 | 2100 |
| 72 hr | − | 100 | 240 | 560 | 600 |
| | + | 220 | 430 | 800 | 840 |
| 96 hr | − | 90 | 180 | 200 | 380 |
| | + | 120 | 160 | 280 | 440 |

Adult worms were recovered from the peritoneal cavity of *Brugia malayi* infected jirds. Two worms were incubated for each concentration in duplicate and incubated at 37° C. in an atmosphere of 5% $CO_2$ and 95% air. Mf counts were taken in 10 ul of spent medium and calculated for 1 ml.
Results from two experiments in duplicate
FCS—fetal calf serum
Mf—microfilariae
MDC—monodansyl cadaverine

D. Effect of Monodansyl Cadaverine on Microfilariae Release In Vitro by *Brugia pahangi* Adult Female Nematodes Adult female *Brugia pahangi* nematodes were obtained from the peritoneal cavities of one hundred twenty-day old infected jirds, rinsed thoroughly in RPMI 1640 medium which was supplemented with ten percent fetal calf serum, twenty millimolar hepes buffer, one hundred units per milliliter of penicillin and one hundred micrograms per milliliter of streptomycin. Two female nematodes were incubated, for each concentration of monodansyl cadaverine, either one hundred or two hundred micromolar, in this supplemented RPMI 1640 medium. The control nematodes, without monodansyl cadaverine, and the nematodes in one milliliter of the supplemented RPMI 1640 medium plus the monodansyl cadaverine were incubated for a period of one to four days at thirty-seven degrees Celsius in an atmosphere of five percent carbon dioxide and ninety-five percent air. Microfilariae counts were taken after the one to four day incubation in ten microliter aliquots of spent medium and calculated for one milliliter. Each piece of data in Table VI is a mean of two experiments in duplicate.

The results of this experiment can be seen in Table VI. Two hundred micromolar concentration of monodansyl cadaverine inhibits the production of microfilariae in *Brugia pahangi* after the first day of treatment, in vitro.

TABLE VI

Effect of MDC on Microfilariae release in vitro by *Brugia pahangi* adult female nematodes

| MDC | 10% FCS | Mf counts in 1 ml of spent medium (Mean of 2 experiments in duplicate) Days of incubation | | | |
|---|---|---|---|---|---|
| | | Day 1 | Day 2 | Day 3 | Day 4 |
| 0 (Controls) | − | 2800 | 3200 | 3100 | 3100 |
| | + | 4200 | 4400 | 4400 | 4500 |

TABLE VI-continued

Effect of MDC on Microfilariae release in vitro by *Brugia pahangi* adult female nematodes

| MDC | 10% FCS | Mf counts in 1 ml of spent medium (Mean of 2 experiments in duplicate) Days of incubation | | | |
|---|---|---|---|---|---|
| | | Day 1 | Day 2 | Day 3 | Day 4 |
| 100 uM | − | 500 | 540 | 560 | 500 |
| | + | 1000 | 980 | 1000 | 1100 |
| 200 uM | − | 0 | 0 | 0 | 0 |
| | + | 20 | 28 | 30 | 30 |

Adult nematodes were recovered from the peritoneal cavity of *Brugia pahangi* infected jirds. Two nematodes were incubated for each concentration in duplicate and incubated at 37° C. in an atmosphere of 5% $CO_2$ and 95% air. Mf counts were taken in 10 ul of spent medium and calculated for 1 ml.
FCS—fetal calf serum
Mf—microfilariae
MDC—monodansyl cadaverine

E. Effect of Monodansyl Cadaverine on Microfilariae Release in vitro by *Brugia patei* Adult Female Nematodes Adult female *Brugia patei* nematodes were obtained and treated as recited in Example ID.

The results can be seen in Table VII. Incubation of *Brugia patei* adult female nematodes with monodansyl cadaverine at the two hundred micromolar concentration level prevents the release and production of mature microfilariae of *Brugia patei*, in vitro after twenty-four hours.

TABLE VII

Effect of MDC on Mf release in vitro by *Brugia patei* adult female nematodes

| MDC | 10% FCS | Mf counts in 1 ml of spent medium (Mean of 2 experiments in duplicate) Days of incubation | | | |
|---|---|---|---|---|---|
| | | Day 1 | Day 2 | Day 3 | Day 4 |
| 0 (Controls) | − | 900 | 920 | 950 | 930 |
| | + | 1100 | 1200 | 1220 | 1200 |
| 100 uM | − | 600 | 640 | 620 | 640 |
| | + | 800 | 820 | 830 | 850 |
| 200 uM | − | 0 | 0 | 0 | 0 |
| | + | 14 | 24 | 26 | 25 |

Adult nematodes were recovered from the peritoneal cavity of *Brugia patei* infected jirds. Two nematodes were incubated for each concentration in duplicate and incubated at 37° C. in an atmosphere of 5% $CO_2$ and 95% air. Mf counts were taken in 10 ul of spent medium and calculated for 1 ml.
FCS—fetal calf serum
Mf—microfilariae
MDC—monodansyl cadaverine

F. Detection of Transglutaminase in Adult Female *Brugia malayi* Nematodes by Western Blot Analysis Adult nematodes were obtained from the peritoneal cavities of infected Mongolian jirds as described in Example IA. Fifteen male and fifteen female nematodes were immediately rinsed three times in twenty millimolar Tris-buffered saline (pH 7.6), sonicated for thirty seconds in four hundred microliters of the same Tris buffer containing one millimolar EDTA, one hundred fifty millimolar sodium chloride, one and five-tenths millimolar beta-mercaptoethanol and one millimolar phenylmethylsulphonyl fluoride. The sonicates were microfuged for five minutes and the supernatants were recovered and referred to as the soluble fraction. The pellet was resuspended in two hundred microliters of one-tenth percent (v/v) zwitterionic detergent, 3-[(3-chloramidopropyl)dimethylammino]-1-propane sulfonate (CHAPS) in Tris-buffered saline, sonicated and referred to as the insoluble fraction.

The soluble and insoluble fractions were each mixed with SDS sample buffer containing five percent beta-mercaptoethanol and boiled. Fifty micrograms of each were electrophoresed on a four to twenty percent polylyacrylamide-gradient gel and then transferred to nitrocellulose. Immunodetection of transglutaminase on nitrocellulose paper was performed using as anti-tissue transglutaminase monoclonal antibody (CUB 7401) and alkaline-phosphatase-coupled goat antibody to mouse immunoglobulin G (Promega) as second antibody (7). Lane 1: MW markers; Lane 2: one microgram of purified guinea pig liver transglutaminase; Lane 3: extracts from male nematodes; Lane 4: soluble extracts from female nematodes; Lane 5: insoluble extracts from female nematodes.

The results of the immunoblot analysis of male and female nematode proteins can be seen in FIG. 2A. Monoclonal antibody (CUB 7401) against tissue-type transglutaminase revealed the presence of a single major immunoreactive band at 22 kD in the soluble extracts from female nematodes, as seen in FIG. 2A, Lane 4. Immunoblots of the insoluble fraction from the female nematodes reacted weakly but consistently with anti-transglutaminase antibody. Extracts from male nematodes showed no detectable band indicating the lack of a transglutaminase enzyme, FIG. 2A, Lane 3.

G. Detection of Transglutaminase in Adult Female Brugia malayi Nematodes by Immunoprecipitation Male and female Brugia malayi nematodes, freshly obtained as in Example IA, were metabolically labeled by culture for one hour in methionine/cysteine-free medium containing two hundred microcuries per milliliter of Tran-[$^{35}$S] label (ICN Biomedicals). The labeled parasite extracts were immunoprecipitated with CUB 7401 antibody and the immune-complexes were fractionated by SDS-gel electrophoresis, and detected by fluorography. FIG. 2B. Lane 1: immunoprecipitate from male nematodes; Lane 2: immunoprecipitate from female nematodes; Lane 3: insoluble extracts from female nematodes.

Immunoprecipitates from adult nematodes pulse labeled with [$^{35}$S] methionine confirmed the identity and pattern of transglutaminase in the soluble and insoluble fractions of female nematodes, whereas the immunoprecipitate from the male nematodes showed no detectable band at the 22 kD position.

H. Total Protein Profiles of Adult Brugia malayi Nematodes

Adult Brugia malayi nematodes were obtained as described in Example IA. Adult nematodes were treated as described in Example IF to obtain the soluble and insoluble fractions. These fractions were each mixed with SDS sample buffer containing five percent betamercaptoethanol and boiled. Fifty micrograms of each were electrophoresed on a four to twenty percent continuous PAGE, followed by protein staining with Coomassie blue. FIG. 2C illustrates the results. Line 1: Five micrograms of purified liver transglutaminase; Lane 2: adult male nematodes; Lane 3: adult female nematodes soluble fraction; Lane 4: adult female nematodes insoluble fraction; Lane 5: molecular weight markers.

Comparison of the Coomassie blue profile of male and female adult nematodes (FIG. 2C) revealed some differences in the protein bands; therefore differences in total protein profiles of the two sexes exists.

I. Indirect Immunofluorescence Labeling of Brugia malayi Female Nematodes

Nematode specimens freshly obtained as detailed in Example IA were immediately fixed on slides in pre-chilled ethanol:acetic acid (3:1) for five minutes, permeablized with one-tenth percent CHAPS in phosphate buffered saline (PBS), stained with monoclonal antibody to tissue transglutaminase (CUB 7401), followed by a fluorescein isothiocyanate (FITC)-labeled goat antibody to mouse immunoglobulin G (Sigma). A drop of p-phenylene-diamine in a mixture of PBS and glycerol (1:9) was added and cover slips were applied. The slides were examined under a Leitz phase-contrast, FIG. 3A, and a fluorescence microscope, FIG. 3B, using 40× objective.

Figure 3B:
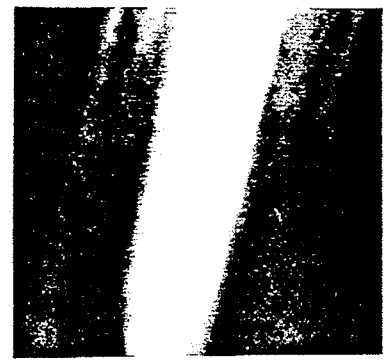

Indirect immunofluorescence staining of female nematodes, FIGS. 3A and 3B, with CUB 7401 antibody followed by a FITC-conjugated anti-mouse IgG, elicited a distinct immunofluorescence pattern. In control experiments, normal mouse serum, supernatant from a control hybridoma clone CUB 11 or second antibody alone failed to produce immunofluorescence (data not shown).

Figure 4A:
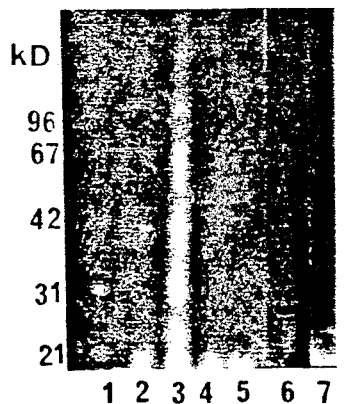
FIGS. 4A and 4B represent detection of substrate proteins used by exogenous guinea pig liver transglutaminase and endogenous transglutaminase in *Brugia malayi* adult male and female nematodes.
Figure 4B:
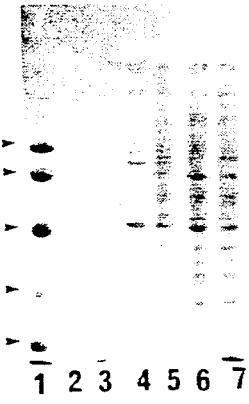

J. Detection of Substrate Proteins Used by Exogenous and Endogenous Transglutaminases Freshly obtained male and female Brugia malayi adult nematodes as described in Example IA were sonicated in buffer solution as described in Example IF. FIG. 4A illustrates detection of substrate proteins for various transglutaminases. Two hundred fifty microgram aliquots from male (Lane 2 and Lane 4) and female (Lane 3 and Lane 5) extracts were incubated with five micrograms of liver (exogenous) transglutaminase (Lane 2 and Lane 3) at thirty-seven degrees Celsius in a final volume of two hundred microliter reaction mixtures containing fifty millimolar Tris-HCl (pH 7.5), three hundred millimolar sodium chloride, fifteen millimolar beta-mercaptoethanol, two hundred micromolar monodansyl cadaverine and five millimolar of either calcium chloride (Lane 2 and Lane 3) or EGTA (Lane 4 and Lane 5). After thirty minutes incubation, the reaction was stopped by the addition of SDS-sample buffer. The samples were boiled, and fifty (Lane 2 and Lane 3) or one hundred (lane 4 and Lane 5) micrograms of the extract were separated on a ten percent SDS-polyacrylamide gel. Transglutaminase-catalyzed conjugation of proteins to monodansyl cadaverine was visualized under UV light. Proteins which served as substrates for endogenous transglutaminase (Lane 6) were detected by incubating the freshly isolated female nematodes for twenty-four hours at thirty-seven degrees Celsius in RPMI 1640 medium containing ten percent fetal calf serum with or without two hundred micromolar monodansyl cadaverine. At the end of the incubation period, the nematodes were removed and thoroughly washed in Tris buffer (twenty millimolar, pH 2.5), sonicated for thirty seconds and microfuged. The supernatants were then subjected to SDS-PAGE and the proteins which were covalently conjugated to monodansyl cadaverine were visualized under UV light (8). Extracts from untreated female nematodes served as the control (Lane 7). Lane 1 contains the molecular weight markers. FIG. 4B is the Coomassie blue stained gel of the protein sample shown in FIG. 4A.

Results from this study are shown in FIGS. 4A and 4B. Extracts from male and female nematodes contained several proteins which served as substrates for purified liver tissue transglutaminase. Nevertheless, in female nematodes the number and amount of substrate proteins was much higher than those present in male nematodes (FIG. 4, Lane 3 versus Lane 2). Conjugation of monodansyl cadaverine to nematode proteins was completely blocked in the presence of EGTA (FIG. 4, Lane 4 and Lane 5), suggesting the requirement for calcium ions ($Ca^{+2}$) for the enzymatic activity. In order to identify the parasitic nematode proteins used as substrates by endogenous transglutaminase, the in situ conjugation of monodansyl cadaverine in live female nematodes was studied. Fractionation of extracts from monodansyl cadaverine treated female nematodes on SDS-PAGE and visualization under UV light, revealed the presence of a major monodansyl cadaverine corrugated fluorescent band at 65 kD (FIG. 4, Lane 6). In addition, several other minor bands were detected ranging from 15 kD to 150 kD molecular weight. The bands at 21, 42, 45, 55 and 130 kD were relatively prominent. Control extracts from untreated female nematodes failed to show any fluorescent band under UV light (FIG. 4A, Lane 7).

EXAMPLE II

In Vivo Transglutaminase Inhibition in *Brugia malayi*

Preliminary studies utilizing a tranglutaminase inhibitor, monodansyl cadaverine [N-(5-aminopentyl)-5-dimethylamino-1-naphthalenesulfonamide] to treat *Brugia malayi* nematodes within a mammalian host indicated that the filarial infection can be controlled, if not eliminated, in the host.

A monodansyl cadaverine toxicity study was performed which showed that levels of the transglutaminase inhibitor far exceeding the desired dosage necessary to treat the filiarial infection in humans or other animals produced little if any toxicity, and were filariacidal.

For treatment, the transglutaminase inhibitor, preferably monodansyl cadaverine [N-(5-aminopentyl)-5-dimethylamino-1-naphthalenesulfonamide], but not limited to only this pseudo-substrate, may be formulated into pharmaceutical compositions and administered using a compatible therapeutic regimen. With the aid of the present disclosure, those of skill in the art should be able to derive suitable dosages and schedules of administration for any number of effective compositions containing a transglutaminase inhibitor. A preferred dosage might be that which is sufficient to achieve an effective blood concentration of greater than about a 300 micromolar level. The dosage in an average person might be in the range of no more than 6 mg/Kg body weight. Determination of effective amounts of transglutaminase inhibitor, however, should be determined by those of skill in the art.

In addition to the transglutaminase inhibitor, the pharmaceutical compositions may contain any number of acceptable pharmaceutical excipients and auxiliaries that facilitate process of the active compounds into the preparations that can be used pharmaceutically. As previously indicated, preparations may be designated for parenteral, transdermal or enteral administration to mammalian hosts, e.g. humans. Suitable formulations for parenteral administration include aqueous solutions of the active compounds in water soluble or water dispersible form. Sometimes, suspensions of active compounds may be administered in suitable lipophilic carriers. The pharmaceutical formulations may contain substances which increase viscosity, for example, sodium carboxymethyl cellulose, sorbitol and/or dextran. Optionally, the formulation may also contain stabilizers. With each formulation, suitable excipients such as saline, lipids or physiologic buffers, known to those of skill in the art, may be used.

A. In Vivo Effect of Monodansyl Cadaverine on Survival of *Brugia malayi* Adult Nematodes The effect of intraperitoneal doses of monodansyl cadaverine on transplanted *Brugia malayi* adult female nematodes which were transplanted intraperitoneally into nude mice was studied. Six nude mice were taken as the control group and each transplanted intraperitoneally with five adult female *Brugia malayi* nematodes. Four weeks after the transplantation the animals were sacrificed and the nematodes recovered. For the monodansyl cadaverine test group, eight nude mice were each transplanted intraperitoneally with five *Brugia malayi* adult female nematodes. A week after transplantation, these animals were treated intraperitoneally with monodansyl cadaverine (two-tenths of a milliliter of a ten millimolar solution) three times per week for one week. Two weeks after the last monodansyl cadaverine treatment the animals were sacrificed and the nematodes were recovered and counted.

A significant difference in the number of viable nematodes existed between the control group and the group treated with monodansyl cadaverine. Some nematode loss may be accorded to natural rejection, about 1.5 fold difference in the original number of nematodes transplanted per animal versus the number of nematodes per animal at the completion of the experiment. This does not account for the 13 fold difference in the number of nematodes in the control animals versus the number of nematodes per animal treated. Monodansyl cadaverine is obviously very effective in reducing the viability of the *Brugia malayi* nematodes. These results can be seen in Table VIII. The concentration of monodansyl cadaverine administered to each mouse was about five times greater than the concentration necessary, in vitro, to prevent microfilariae development in utero in the adult *Brugia malayi* female nematodes.

TABLE VIII

In vivo effect of MDC on survival of *Brugia malayi* adult Nematodes

| Treatment with MDC (I/P) | No. of Animals | Total Nematodes | X Nematodes/ Animal |
|---|---|---|---|
| None (Control) | 6 | 20 (4/6)* | 3.3 |
| days 1, 3, 5 | 8 | 2 (2/8)* | 0.25 |

*Number of animals with adult nematodes per number of animals tested.
5 adult nematodes each were transplanted into nude mice intraperitoneally (I/P). A week after the transplantation, animals were injected intraperitoneally with MDC (0.2 ml of 10 mM solution) three times in one wek on alternte days. Two weeks after the last treatment, animals were sacrificed and nematodes were recovered and counted.
MDC—monodansyl cadaverine

B. In Vivo Toxicity of Monodansyl Cadaverine in CD-1 Mice

Four groups of four male CD-1 mice were studied for toxic reactions due to administeration of varying amounts of monodansyl cadaverine (MDC) either intravenously or intraperitoneally (Table IX). Each mouse was four months old and weighed forty to fifty grams. Measured aliquots were taken from a ten millimolar stock solution of monodansyl cadaverine in saline, pH 2.5, and injected into the mice. Group 1 mice were given a two-tenths of a milliliter bolus intravenously of the ten millimolar stock solution. This dose is equivalent to 0.670 mg MDC per mouse or 14.8 mg per Kg of body weight. No toxicity was observed at this dose in any of the animals. Group 2 mice were given a three-tenths of a milliliter bolus intravenously of the ten millimolar MDC stock solution. This dose is equivalent to 1.0 mg MDC per mouse or 22.3 mg per Kg of body weight. No toxicity was observed at this dose in any of the animals. Group 3 mice were given a five-tenths of a milliliter bolus of the ten millimolar stock solution intravenously. This dose is equivalent to 1.675 mg MDC per mouse or 37.22 mg per Kg of body weight. Immediately after this injection the animals showed a definite decline in activity but recovered normal activity rate within a few seconds and no deaths were observed. Group 4 mice were injected with a seven-tenths of a milliliter bolus of the 10 millimolar MDC stock solution intraperitoneally. This dose was equivalent to 2.345 mg per mouse or 52.1 mg per Kg of body weight. No toxicity was observed. Twelve days later all mice were alive and showed no toxic effects from the MDC.

TABLE IX

In vivo Toxicity Study of MDC in CD-1 Mice

| Group (4 mice each) | Amount of 10 mM MDC | IV or IP | mg MDC per mouse | mg MDC per Kg body weight | Toxic Reaction |
|---|---|---|---|---|---|
| 1 | 0.2 ml | IV | 0.670 | 14.80 | NONE |
| 2 | 0.3 ml | IV | 1.000 | 22.30 | NONE |
| 3 | 0.5 | IV | 1.675 | 36.22 | ACTIVITY DECLINE FOR FEW SECONDS |
| 4 | 0.7 | IP | 2.345 | 52.10 | NONE |

MDC—monodansyl cadaverine
IV—intravenously
IP—intraperitoneally

The results of the in vivo toxicity study indicated that the concentration of monodansyl cadaverine necessary to inhibit microfilariae production in adult female filarial nematodes is about five times less than the minimum dose used in the toxicity study which had no adverse effects on the mammalian host. The dose range of monodansyl cadaverine necessary to be filariacidal is also less than the minimum dose range for the toxicity study.

The foregoing description of the invention has been directed to particular preferred embodiments in accordance with the requirements of the patent statutes and for purposes of explanation and illustration. It will become apparent to those of skill in the art that modifications and changes may be made without departing from the scope and the spirit of the invention.

The literature references in the following list are incorporated in pertinent part by reference herein for the reasons cited in the text.

REFERENCES

1. Piessens, W. F. and Partono, F., Semin. Infect. Dis., 3, 131 (1980).
2. Nelson, Nature, 300, 1136 (1979).
3. Plorde, J. J., in *Harrison's Principles of Internal Medicine*, Braunwald, Isselbacher, Petersdorf, Wilson, Martin and Fauci, eds. McGraw-Hill, Inc., New York, N.Y. (1987) p. 807–810.
4. Goodwin, L. G., Trans. Roy. Soc. Trop. Med. Hyg., 78 (Suppl.), 1 (1984).
5. Lorand, L. et al., Biochemistry, 7, 1214 (1968).
6. Davis, P. J. A. et al., Diabetes Care, 7, 35(1984).
7. Khera, V. and Mehta, K., J. Leukocyte Biol., 45, 434(1989).
8. Lorand, L. et al., Anal. Biochem., 93, 453 (1979).
9. Ewert, A., in *Medical Microbiology*, S. Baron, ed., Addison-Wesley Publishing Company, Inc., Menlo Park, Calif. (1986) p. 1125–1134.

What is claimed is:

1. A method for inhibiting maturation and production of microfilariae by female filarial nematodes residing in a mammalian host comprising administering to a mammalian host monodansyl cadaverine, methylamine, histamine, or putrescine in an amount inhibiting transglutaminase activity and maturation and microfilariae production of resident female filarial nematodes.

2. The method of claim 1 wherein the filarial nematode is *Brugia pahangi, Brugia patei,* or *Brugia timori.*

3. The method of claim 1 wherein the filarial nematode is *Wuchereria bancrofti.*

4. The method of claim 1 wherein the filarial nematode is *Loa loa.*

5. The method of claim 1 wherein the filarial nematode is *Onchocerca volvulus.*

6. The method of claim 1 wherein the amount of monodansyl cadaverine, methylamine, histamine, or putrescine results in about a 200 micromolar concentration in the host.

7. A method for inhibiting maturation and production of microfilariae by *Brugia malayi* residing in a mammalian host comprising treating an adult female *Brugia malayi* nematode in said mammalian host with monodansyl cadaverine, methylamine, histamine, or putrescine in an amount sufficient to inhibit transglutaminase activity, and maturation and microfilariae production of said *Brugia malayi.*

8. The method of claims 1 or 3 wherein monodansyl cadaverine is administered.

9. The method for inhibiting in vitro maturation and production of microfilariae by a *Brugia malayi, Brugia pahangi* or *Brugia patei* nematode comprising treating an adult female *Brugia malayi, Brugia pahangi* or *Brugia patei* nematode with monodansyl cadaverine, methylamine, histamine, or putrescine in an amount sufficient to inhibit transglutaminase activity of said nematode.

10. The method of claim 9 wherein the nematode is treated with monodansyl cadaverine.

11. A method for treating lymphatic filariasis in a mammalian host comprising administering monodansyl cadaverine, methylamine, histamine or putrescine to said host in an amount sufficient to kill adult filarial nematodes producing lymphatic filariasis.

12. A method for treating lymphatic filariasis produced by *Brugia malayi* in a mammalian host comprising administering monodansyl cadaverine, methylamine, histamine or putrescine to said host in an amount sufficient to kill adult *Brugia malayi* nematodes producing the lymphatic filariasis.

13. The method of claims 1, 11 or 12 wherein the monodansyl cadaverine, methylamine, histamine or putrescine is parenterally administered to a mammalian host.

14. The method of claims 1, 11 or 12 wherein the monodansyl cadaverine, methylamine, histamine or putrescine is administered to a mammalian host enterally.

15. The method of claim 11 wherein the adult filarial nematode producing the lymphatic filariasis is *Brugia*

*pahangi, Brugia patei, Brugia timori* or *Wuchereria bancrofti*.

16. The method of claims 11 or 12 wherein the transglutaminase inhibitor is monodansyl cadaverine.

17. The method of claims 1, 11 or 12 wherein the mammalian host is a rodent.

18. The method of claims 1, 11 or 12 wherein the mammalian host is a human.

* * * * *

UNITED STATES PATENT AND TRADEMARK OFFICE
CERTIFICATE OF CORRECTION

PATENT NO. : 5,124,358
DATED : January 16, 1990
INVENTOR(S) : Mehta, et al

It is certified that error appears in the above-indentified patent and that said Letters Patent is hereby corrected as shown below:

On the Title Page, Item [75] "Mehta Kapil" should read —Kapil Mehta—.

On the Title Page, Item [73] in addition to "The Board of Regents, The University of Texas System, Austin, Tex.", should also be listed —The University of South Florida, Tampa, Florida—.

Column 13, line 59, "Line" should read —Lane—.

Signed and Sealed this

Twenty-fifth Day of October, 1994

Attest:

BRUCE LEHMAN

*Attesting Officer*    *Commissioner of Patents and Trademarks*